(12) United States Patent
Zhu et al.

(10) Patent No.: US 10,668,293 B2
(45) Date of Patent: *Jun. 2, 2020

(54) SYSTEM AND METHOD FOR ESTIMATING LOCATION AND DEPTH OF STIMULATION LEADS

(71) Applicant: Boston Scientific Neuromodulation Corporation, Valencia, CA (US)

(72) Inventors: Changfang Zhu, Valencia, CA (US); Kerry Bradley, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 236 days.

This patent is subject to a terminal disclaimer.

(21) Appl. No.: 15/860,241

(22) Filed: Jan. 2, 2018

(65) Prior Publication Data
US 2018/0117343 A1   May 3, 2018

Related U.S. Application Data

(63) Continuation of application No. 13/796,022, filed on Mar. 12, 2013, now Pat. No. 9,872,992.

(Continued)

(51) Int. Cl.
*A61N 1/372* (2006.01)

(52) U.S. Cl.
CPC ...... *A61N 1/37211* (2013.01); *A61N 1/37247* (2013.01); *A61N 1/37264* (2013.01)

(58) Field of Classification Search
CPC ............ A61N 1/37211; A61N 1/37247; A61N 1/37264

(Continued)

(56) References Cited

U.S. PATENT DOCUMENTS

| 6,516,227 B1 | 2/2003 | Meadows et al. |
| 6,622,048 B1 | 9/2003 | Mann et al. |

(Continued)

FOREIGN PATENT DOCUMENTS

EP   2825256 A2   1/2015

OTHER PUBLICATIONS

"U.S. Appl. No. 13/796,022, Advisory Action dated Oct. 17, 2014", 3 pgs.

(Continued)

*Primary Examiner* — Christopher A Flory
(74) *Attorney, Agent, or Firm* — Schwegman Lundberg & Woessner, P.A.

(57) ABSTRACT

A method and external control device for performing a medical procedure on a patient in which at least one stimulation lead is implanted. An electrical signal is conveyed from the stimulation lead into tissue of the patient. An electrical parameter indicative of tissue impedance is measured in response to the conveyance of the electrical signal. One of a plurality of different anatomical regions in which the stimulation lead is implanted is selected and/or a depth in which the stimulation is implanted is determined based on the measured electrical parameter. A stimulation parameter is defined based on the selected one anatomical region and/or implantation depth. Electrical stimulation energy from the stimulation lead is conveyed into the one determined anatomical region in accordance with the defined stimulation parameter.

20 Claims, 10 Drawing Sheets

Related U.S. Application Data

(60) Provisional application No. 61/611,840, filed on Mar. 16, 2012.

(58) Field of Classification Search
USPC .......................................... 607/58, 59, 117
See application file for complete search history.

(56) References Cited

U.S. PATENT DOCUMENTS

| | | | |
|---|---|---|---|
| 6,895,280 | B2 | 5/2005 | Meadows et al. |
| 6,993,384 | B2 | 1/2006 | Bradley et al. |
| 7,239,920 | B1 | 7/2007 | Thacker et al. |
| 7,317,948 | B1 | 1/2008 | King et al. |
| 7,343,200 | B2 | 3/2008 | Litvak et al. |
| 7,539,538 | B2 | 5/2009 | Parramon et al. |
| 7,650,184 | B2 | 1/2010 | Walter |
| 8,019,439 | B2 | 9/2011 | Kuzma et al. |
| 8,131,357 | B2 | 3/2012 | Bradley et al. |
| 8,355,797 | B2 * | 1/2013 | Caparso ............. A61N 1/36071 607/62 |
| 8,660,653 | B2 | 2/2014 | Kothandaraman |
| 8,909,350 | B2 | 12/2014 | Lee |
| 8,977,360 | B2 | 3/2015 | Kim et al. |
| 9,235,685 | B2 * | 1/2016 | McIntyre ........... A61N 1/36082 |
| 9,872,992 | B2 | 1/2018 | Zhu |
| 2003/0139781 | A1 | 7/2003 | Bradley et al. |
| 2005/0267546 | A1 | 12/2005 | Parramon et al. |
| 2006/0224222 | A1 | 10/2006 | Bradley |
| 2007/0150036 | A1 | 6/2007 | Anderson |
| 2007/0168004 | A1 | 7/2007 | Walter |
| 2007/0168007 | A1 | 7/2007 | Kuzma et al. |
| 2009/0018403 | A1 * | 1/2009 | Black .................. A61B 5/0031 600/300 |
| 2009/0210208 | A1 * | 8/2009 | McIntyre ........... A61N 1/36082 703/11 |
| 2010/0010566 | A1 | 1/2010 | Thacker et al. |
| 2010/0121409 | A1 | 5/2010 | Kothandaraman et al. |
| 2011/0046697 | A1 | 2/2011 | Gerber et al. |
| 2011/0054556 | A1 | 3/2011 | Chow |
| 2011/0106215 | A1 | 5/2011 | Moffitt |
| 2012/0016447 | A1 | 1/2012 | Zhu et al. |
| 2012/0035439 | A1 * | 2/2012 | Ferren .................. A61B 1/041 600/302 |
| 2012/0109230 | A1 | 5/2012 | Kothandaraman et al. |
| 2013/0245719 | A1 | 9/2013 | Zhu et al. |

OTHER PUBLICATIONS

"U.S. Appl. No. 13/796,022, Appeal Brief filed Dec. 5, 2014", 17 pgs.
"U.S. Appl. No. 13/796,022, Appeal Decision dated Aug. 2, 2017", 9 pgs.
"U.S. Appl. No. 13/796,022, Examiners Answer dated Mar. 6, 2015", 7 pgs.
"U.S. Appl. No. 13/796,022, Final Office Action dated Jul. 30, 2014", 11 pgs.
"U.S. Appl. No. 13/796,022, Non Final Office Action dated. Apr. 10, 2014", 10 pgs.
"U.S. Appl. No. 13/796,022, Notice of Allowance dated Sep. 15, 2017", 8 pgs.
"U.S. Appl. No. 13/796,022, Response filed Feb. 20, 2014 to Restriction Requirement dated Jan. 28, 2014", 6 pgs.
"U.S. Appl. No. 13/796,022, Response filed Jun. 6, 2014 to Non Final Office Action dated Apr. 10, 2014", 9 pgs.
"U.S. Appl. No. 13/796,022, Response filed Oct. 3, 2014 to Final Office Action dated Jul. 30, 2014", 8 pgs.
"U.S. Appl. No. 13/796,022, Restriction Requirement dated Jan. 28, 2014", 9 pgs.
"European Application Serial No. 13712443.4, Communication Pursuant to Article 94(3) EPC dated Oct. 30, 2017", 3 pgs.
"International Application Serial No. PCT/US2013/030446, International Preliminary Report on Patentability dated Sep. 25, 2014", 8 pgs.
"International Application Serial No. PCT/US2013/030446, International Search Report dated Sep. 18, 2013", 5 pgs.
"International Application Serial No. PCT/US2013/030446, Written Opinion dated Sep. 18, 2013", 6 pgs.
"European Application Serial No. 13712443.4, Response filed Mar. 9, 2018 to Communication Pursuant to Article 94(3) EPC dated Oct. 30, 2017", 3 pgs.

\* cited by examiner

SYSTEM AND METHOD FOR ESTIMATING LOCATION AND DEPTH OF STIMULATION LEADS

RELATED APPLICATION DATA

The present application is a continuation of U.S. application Ser. No. 13/796,022, filed Mar. 12, 2013, now issued as U.S. Pat. No. 9,872,992, which claims the benefit under 35 U.S.C. § 119 to U.S. provisional patent application Ser. No. 61/611,840, filed Mar. 16, 2012. The foregoing application is hereby incorporated by reference into the present application in its entirety.

FIELD OF THE INVENTION

The present invention relates to tissue stimulation systems, and more particularly, to a system and method for stimulating nerve fibers.

BACKGROUND OF THE INVENTION

Implantable stimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) techniques, which directly stimulate the spinal cord tissue of the patient, have long been accepted as a therapeutic modality for the treatment of chronic pain syndromes, and the application of spinal cord stimulation has begun to expand to additional applications, such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, Functional Electrical Stimulation (FES) systems such as the Freehand system by NeuroControl (Cleveland, Ohio) have been applied to restore some functionality to paralyzed extremities in spinal cord injury patients. Occipital Nerve Stimulation (ONS), in which leads are implanted in the tissue over the occipital nerves, has shown promise as a treatment for various headaches, including migraine headaches, cluster headaches, and cervicogenic headaches. In recent investigations, Peripheral Stimulation (PS), which includes Peripheral Nerve Field Stimulation (PNFS) techniques that stimulate nerve tissue directly at the symptomatic site of the disease or disorder (e.g., at the source of pain), and Peripheral Nerve Stimulation (PNS) techniques that directly stimulate bundles of peripheral nerves that may not necessarily be at the symptomatic site of the disease or disorder, has demonstrated efficacy in the treatment of chronic pain syndromes and incontinence, and a number of additional applications are currently under investigation.

Each of these implantable stimulation systems typically includes an electrode lead implanted at the desired stimulation site and neurostimulator (e.g., an implantable pulse generator (IPG)) implanted remotely from the stimulation site, but coupled either directly to the electrode lead or indirectly to the electrode lead via a lead extension. Thus, electrical pulses can be delivered from the neurostimulator to the stimulation lead(s) to stimulate or activate a volume of neural tissue. In particular, electrical energy conveyed between at least one cathodic electrode and at least one anodic electrode creates an electrical field, which when strong enough, depolarizes (or "stimulates") the neurons beyond a threshold level, thereby inducing the firing of action potentials (APs) that propagate along the neural fibers.

Stimulation energy may be delivered to the electrodes during and after the lead placement process in order to verify that the electrodes are stimulating the target neural elements and to formulate the most effective stimulation regimen. The regimen will dictate which of the electrodes are sourcing current pulses (anodes) and which of the electrodes are sinking current pulses (cathodes) at any given time, as well as the amplitude, duration, rate, and burst rate of the stimulation pulses.

The stimulation regimen will typically be one that provides stimulation energy to all of the target tissue that must be stimulated in order to provide the therapeutic benefit, yet minimizes the volume of non-target tissue that is stimulated. In the case of SCS and PS, such a therapeutic benefit is accompanied by "paresthesia," i.e., a tingling sensation that is effected by the electrical stimuli applied through the electrodes.

The stimulation system may further comprise a handheld remote control (RC) to remotely instruct the neurostimulator to generate electrical stimulation pulses in accordance with selected stimulation parameters. The RC may, itself, be programmed by a technician attending the patient, for example, by using a Clinician's Programmer (CP), which typically includes a general purpose computer, such as a laptop, with a programming software package installed thereon. If the IPG contains a rechargeable battery, the stimulation system may further comprise an external charger capable of transcutaneously recharging the IPG via inductive energy.

It is sometimes desirable to use a hybrid stimulation regimen that combines multiple types of stimulation to treat one or more disease conditions. For example, despite many reports of success in relieving radicular pain in the lower extremities and buttocks with SCS, physicians often report difficulties with achieving and maintaining adequate pain control over the long term for patients experiencing axial low back pain, especially for patients experiencing chronic pain due to failed back surgery syndrome (FBSS). Thus, SCS is often inadequate in relieving both the back and leg pain components. However, for patients with chronic low back pain as a result of FBSS, it has been shown that PNFS is extremely effective in reducing pain and enabling patients to resume their normal activities (see Richard M. Paicius, M. D., et al., *Peripheral Nerve Field Stimulation for the Treatment of Chronic Low Back Pain: Preliminary Results of Long-Term Follow-up: A Case Series*, Neuromodulation, Volume 10, Number 3, 2007, and Jason P. Krutsch, M. D., et al., *A Case Report of Subcutaneous Peripheral Nerve Stimulation for the Treatment of Axial Back Pain Associated with Postlaminectomy Syndrome*," Neuromodulation, Volume 11, Number 2, 2008).

Thus, the use of PNFS as an adjunct to SCS may overcome the limitations of SCS, and may be valid option for the treatment of patients whose pain is severe both in the axial back and legs, with the SCS component targeting the radicular pain, and the PNFS more directly and completely relieving the lower back pain. Based on case studies performed on patients, it has been found that a combination of SCS and PNFS to control lower back and leg pain is, indeed, more effective than either modality alone. Thus, it can be concluded that PNFS may be used in combination with SCS as a safe and effective alternative treatment for patients with chronic low back and leg pain (see Clifford A. Bernstein, M. D., et al., *Spinal Cord Stimulation in Conjunction with*

*Peripheral Nerve Field Stimulation for the Treatment of Low Back and Leg Pain: A Case Series*, Neuromodulation, Volume 11, Number 2, 2008).

These hybrid stimulation systems oftentimes utilize a single IPG that delivers the stimulation energy to support the different stimulation regimens, each of which requires a vastly different programming technique and associated programming interface. For example, in SCS, a large number of tightly spaced electrodes are implanted within the epidural space of the patient to stimulate the spinal cord tissue within a high resolution electrical field, whereas in PNFS, a small number of widely spaced apart electrodes are implanted in the subcutaneous tissues of a peripheral region, such as the lower back region, to directly stimulate the peripheral field (i.e., the region of the affected nerves, the cutaneous afferents, or the dermatomal distribution of these nerves, which then converge back within the spinal cord) in the region of pain. Thus, different programming strategies must typically be employed for a single hybrid stimulation system. In order to best program these hybrid stimulation systems, it would be desirable to quickly and automatically determine the anatomical regions of the patient in which the stimulation leads are implanted, so that the proper stimulation regimens can be applied to these anatomical regions.

It would also be desirable to determine the depth of implantation for a stimulation lead, since depending on the anatomy of the targeted stimulation region and the implant depth of the stimulation lead, the patient may experience different sensations during the stimulation. For example, stimulation lead depth plays an important role in PNFS. If the stimulation lead depth is too superficial, the patient may feel discomfort or painful sensations resulting from A-delta or *C fiber* action at a lower amplitude, which reduces the therapeutic stimulation range for the targeted sensory fibers. If the stimulation lead is too deep, muscle activation may result during stimulation, again limiting the therapeutic stimulation range for the target sensory fibers. Conventional techniques, such as fluoroscopy, can be used to determine the stimulation lead depth, but requires bulky instruments and involves ionized radiation.

SUMMARY OF THE INVENTION

In accordance with a first aspect of the present invention, an external control device for use with a stimulation device capable of conveying an electrical signal to a stimulation lead implanted within a patient, and measuring an electrical parameter in response to the conveyance of the electrical signal is provided. In one embodiment, the electrical parameter is measured at another stimulation lead implanted within the patient. The external control device comprises telemetry circuitry configured for communicating with the stimulation device.

The external control device further comprises a processor configured for receiving the measured electrical parameter from the stimulation device via the telemetry circuitry, and selecting one of a plurality of different anatomical regions in which the stimulation lead is implanted based on the measured electrical parameter.

In one embodiment, the processor is configured for comparing the measured electrical parameter to a plurality of threshold ranges, and selecting the one anatomical region from the plurality of different anatomical regions based on the comparison. For example, if the different anatomical regions comprise a spinal epidural space and a peripheral tissue region, the measured electrical parameter can be indicative of a tissue impedance, a first one of the threshold ranges can be relatively low, a second one of the threshold ranges can be relatively high, in which case, the processor may select the anatomical region to be the spinal epidural space if the tissue impedance is within the first threshold range, and select the anatomical region to be the peripheral tissue region if the tissue impedance is within the second threshold range.

The external control device may further comprise a user interface configured for displaying a plurality of different programming screens respectively associated with different anatomical regions of a patient, selecting one of the programming screens corresponding to the selected anatomical region, and allowing a user to define a stimulation parameter (e.g., an electrode combination) using the selected programming screen. The external control device further comprises a controller configured for instructing the stimulation device via the telemetry circuitry to convey electrical stimulation energy from the stimulation lead in accordance with the defined stimulation parameter.

In an optional embodiment, the processor is further configured for computing a confidence rating for the plurality of different anatomical regions based on the measured electrical parameter, in which case, the user interface may be further configured for conveying information to a user identifying the different anatomical regions and associated computed confidence rating, and allowing the user to select the one anatomical region from the plurality of different anatomical regions based on computed confidence rating.

In accordance with a second aspect of the present inventions, a method of performing a medical procedure on a patient in which a stimulation lead is implanted is provided. The method comprises conveying an electrical signal from the stimulation lead into tissue of the patient and measuring an electrical parameter in response to the conveyance of the electrical signal. In one method, the electrical parameter is measured at another stimulation lead implanted within the patient.

The method further comprises selecting one of a plurality of different anatomical regions in which the stimulation lead is implanted based on the measured electrical parameter. In one method, the measured electrical parameter is compared to a plurality of threshold ranges, and the one anatomical region is selected from the plurality of different anatomical regions based on the comparison. For example, if the different anatomical regions comprise a spinal epidural space and a peripheral tissue region, the measured electrical parameter can be indicative of a tissue impedance, a first one of the threshold ranges can be relatively low, a second one of the threshold ranges can be relatively high, and the anatomical region may be selected to be the spinal epidural space if the tissue impedance is within the first threshold range, and selected to be the peripheral tissue region if the tissue impedance is within the second threshold range.

The method further comprises defining a stimulation parameter (e.g., an electrode combination) based on the selected one anatomical region, and conveying electrical stimulation energy from the stimulation lead into the one determined anatomical region in accordance with the defined stimulation parameter. The method optionally comprises computing a confidence rating for the plurality of different anatomical regions based on the measured electrical parameter, conveying information to a user identifying the different anatomical regions and associated computed confidence rating, and allowing the user to select the one anatomical region from the plurality of different anatomical regions based on computed confidence rating.

In accordance with a third aspect of the present inventions, an external control device for use with a stimulation device capable of conveying an electrical signal to a stimulation lead implanted within a patient, and measuring an electrical parameter indicative of tissue impedance in response to the conveyance of the electrical signal is provided. The external control device comprises telemetry circuitry configured for communicating with a stimulation device, and a processor configured for receiving the measured electrical parameter from the stimulation device via the telemetry circuitry, and determining a depth in which the stimulation is implanted based on the measured electrical parameter. In one embodiment, the processor is configured for determining the depth to be shallow if the tissue impedance is relatively high, the depth to be relatively deep if the implied tissue impedance is relatively low, and the depth to be relatively medium if the tissue impedance is relatively medial. In another embodiment, the processor is further configured for comparing the measured electrical parameter to a reference electrical parameter, and determining the depth based on the comparison.

The external control device further comprises a user interface configured for displaying a programming screen containing information of the determined depth, and allowing a user to define a stimulation parameter using the programming screen. The external control device further comprises a controller configured for instructing the stimulation device via the telemetry circuitry to convey electrical stimulation energy from the stimulation lead in accordance with the defined stimulation parameter.

In accordance with a fourth aspect of the present inventions, a method of performing a medical procedure on a patient in which a stimulation lead is implanted (e.g., subcutaneously) is provided. The method comprises conveying an electrical signal from the stimulation lead into tissue of the patient (e.g., tissue in the peripheral region of the patient), and measuring an electrical parameter indicative of tissue impedance in response to the conveyance of the electrical signal, and determining a depth in which the stimulation is implanted based on the measured electrical parameter. The method further comprises defining a stimulation parameter based on the determined depth, and conveying electrical stimulation energy from the stimulation lead into the tissue in accordance with the defined stimulation parameter.

In one method, the depth is determined to be shallow if the tissue impedance is relatively high, the depth is determined to be relatively deep if the implied tissue impedance is relatively low, and the depth is determined to be relatively medium if the tissue impedance is relatively medial. An optional method further comprises conveying a reference electrical signal into the patient, measuring a reference electrical parameter in response to the conveyance of the reference electrical signal, comparing the measured electrical parameter to the measured reference electrical parameter, and determining the depth based on the comparison.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

Figure 1:
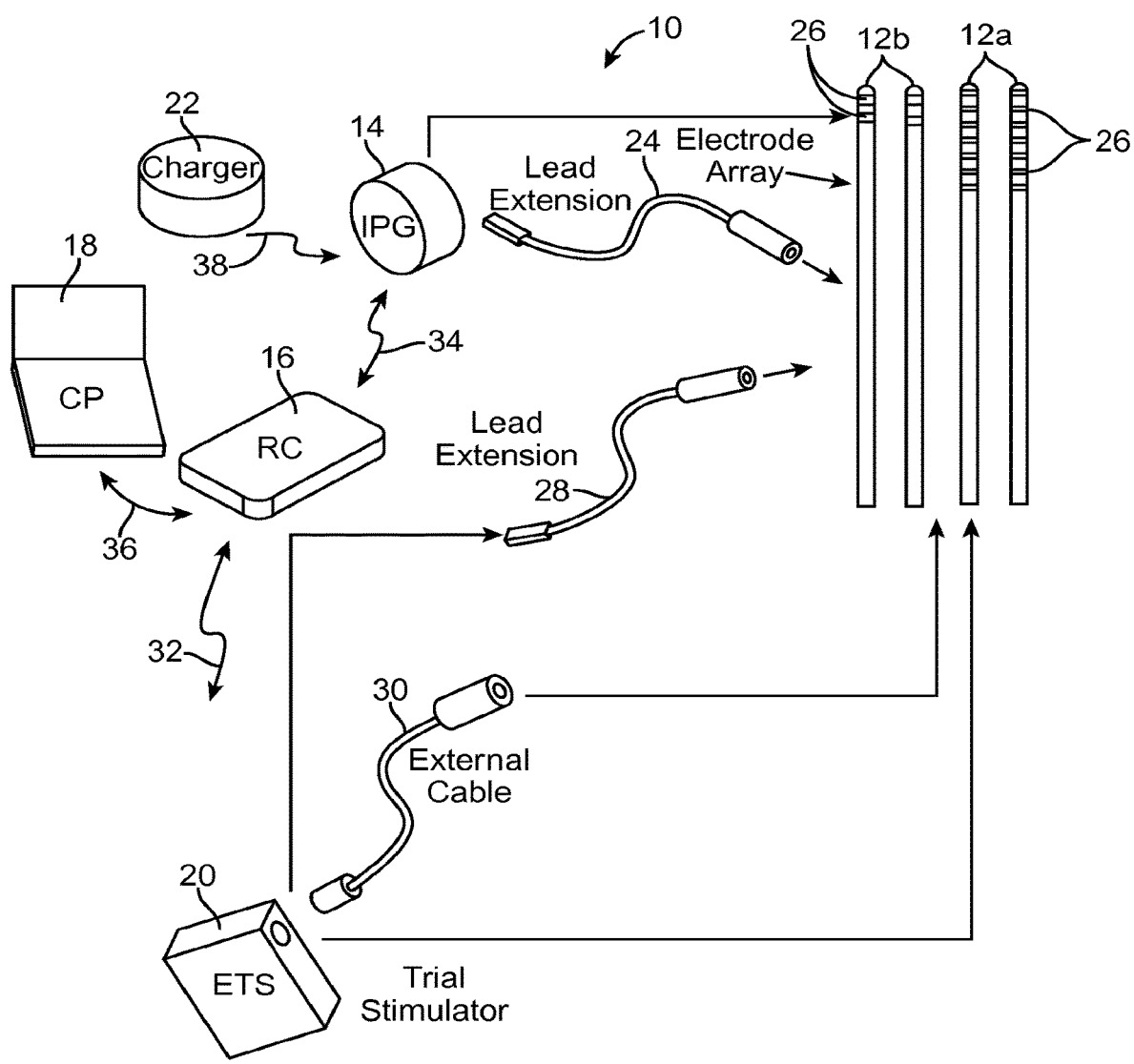
FIG. 1 is plan view of one embodiment of a nerve tissue stimulation system arranged in accordance with the present inventions.

Turning first to FIG. 1, an exemplary nerve tissue stimulation system 10 is used to perform both Spinal Cord Stimulation (SCS) and Peripheral Nerve Field Stimulation (PNFS). The system 10 generally includes a plurality of implantable stimulation leads 12 (at least one stimulation lead for the SCS function and at least one stimulation lead for the PNFS function), a pulse generating device in the form of an implantable pulse generator (IPG) 14, an external control device in the form of a remote controller RC 16, a clinician's programmer (CP) 18, an external trial stimulator (ETS) 20, and an external charger 22.

The IPG 14 is physically connected via one or more lead extensions 24 to the stimulation leads 12, which carry a plurality of electrodes 26 arranged in an array. In the illustrated embodiment, four percutaneous leads 12 (a pair of leads 12*a* for the SCS function and a pair of leads 12*b* for the PNFS function) with a plurality of electrodes 26 are provided. Although four stimulation leads 12 are illustrated, it should be appreciated that less or more stimulation leads 12 can be provided. For example, a single surgical paddle lead can be used for the SCS function and an additional two percutaneous leads 12 can be used for the PNFS function. Or a single stimulation lead 12 (whether a percutaneous lead or a surgical paddle lead) can be used for the SCS function and a single stimulation lead 12 (whether a percutaneous lead or a surgical paddle lead) can be used for the PNFS function. Optionally, the lead extension 24 can be provided with a splitter (not shown), so that a single lead extension can be used to couple the multiple stimulation leads 12 to a single port on the IPG 14. As will be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected via one or more lead extensions 28 and/or one or more external cables 30 to the stimulation leads 12. The ETS 20, which has similar pulse generation circuitry as that of the IPG 14, also delivers electrical stimulation energy in the form of a pulsed electrical waveform to the electrode array 26 in accordance with a set of stimulation parameters. The major difference between the ETS 20 and the IPG 14 is that the ETS 20 is a non-implantable device that is used on a trial basis after the stimulation leads 12 have been implanted and prior to implantation of the IPG 14, to test the responsiveness of the stimulation that is to be provided. Thus, any functions described herein with respect to the IPG 14 can likewise be performed with respect to the ETS 20.

The RC 16 may be used to telemetrically control the ETS 20 via a bi-directional RF communications link 32. Once the IPG 14 and stimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14.

The CP 18 provides clinician detailed stimulation parameters for programming the IPG 14 and ETS 20 in the operating room and in follow-up sessions. The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed stimulation parameters provided by the CP 18 are also used to program the RC 16, so that the stimulation parameters can be subsequently modified by operation of the RC 16 in a stand-alone mode (i.e., without the assistance of the CP 18). The external charger 22 is a portable device used to transcutaneously charge the IPG 14 via an inductive link 38. Once the IPG 14 has been programmed, and its power source has been charged by the external charger 22 or otherwise replenished, the IPG 14 may function as programmed without the RC 16 or CP 18 being present.

For purposes of brevity, the details of the ETS 20 and external charger 22 will not be described herein. Details of exemplary embodiments of these devices are disclosed in U.S. Pat. No. 6,895,280, which is expressly incorporated herein by reference.

Figure 2:
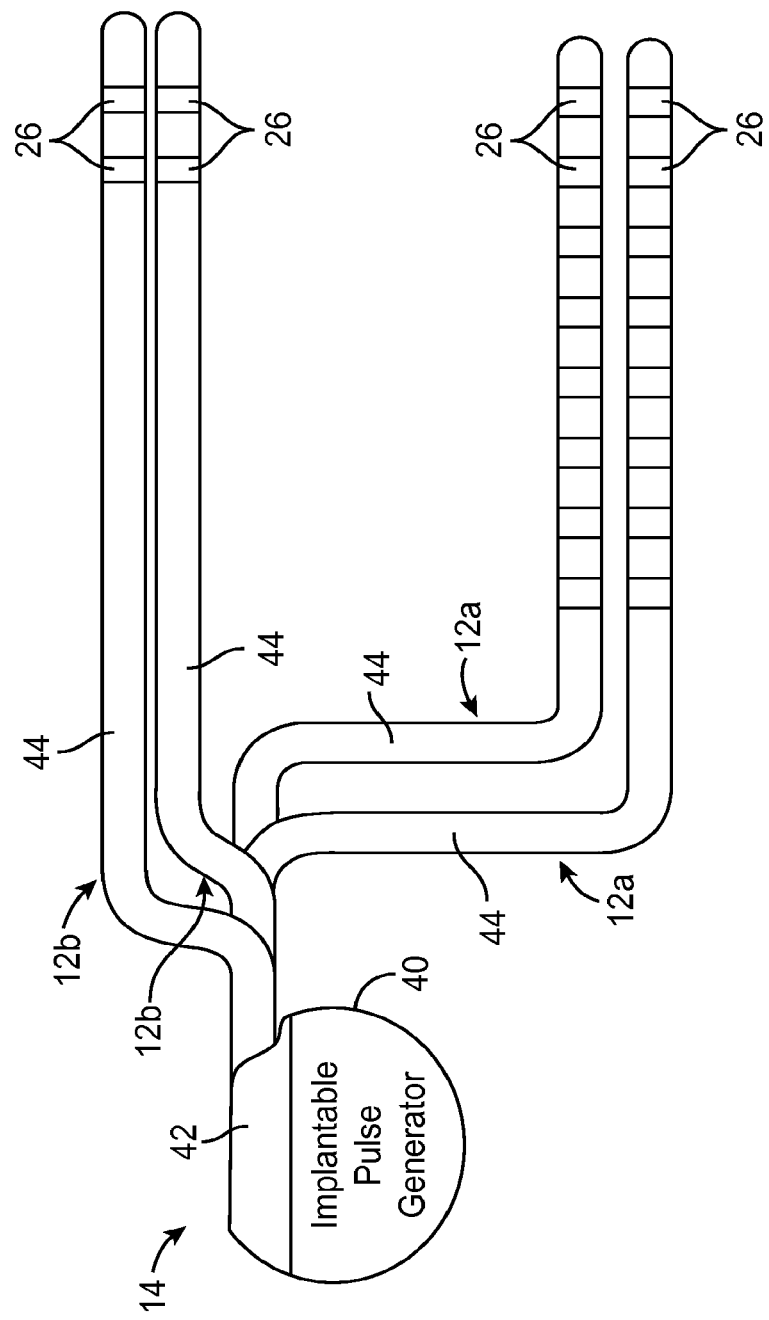
FIG. 2 is a plan view of an implantable pulse generator (IPG) and stimulation leads used in the nerve tissue stimulation system of FIG. 1.

Referring further to FIG. 2, the IPG 14 comprises an outer case 40 for housing the electronic and other components (described in further detail below), and a connector 42 to which the proximal ends of the stimulation leads 12 mate in a manner that electrically couples the electrodes 26 to the internal electronics (described in further detail below) within the outer case 40. The outer case 40 is composed of an electrically conductive, biocompatible material, such as titanium, and forms a hermetically sealed compartment wherein the internal electronics are protected from the body tissue and fluids. In some cases, the outer case 40 may serve as an electrode.

As shown in FIG. 2, each of the percutaneous leads 12 comprises an elongated cylindrical lead body 44, and the electrodes 26 take the form of ring electrodes mounted around the lead body 44. Each of the percutaneous leads 12a has eight electrodes, whereas each of the percutaneous leads 12b has two electrodes. The actual number and shape of leads and electrodes will, of course, vary according to the intended application. For the purposes of describing the embodiments of the present invention, the significance is that the electrode array used for SCS is different from the electrode array used for PNFS, and as such, will require different stimulation regimens. Further details describing the construction and method of manufacturing percutaneous stimulation leads are disclosed in U.S. patent application Ser. No. 11/689,918, entitled "Lead Assembly and Method of Making Same," and U.S. patent application Ser. No. 11/565,547, entitled "Cylindrical Multi-Contact Electrode Lead for Neural Stimulation and Method of Making Same," which are expressly incorporated herein by reference. In alternative embodiments, surgical paddle leads can be utilized, the details of which are disclosed in U.S. patent application Ser. No. 11/319,291, entitled "Stimulator Leads and Methods for Lead Fabrication," which is expressly incorporated herein by reference.

As will be described in further detail below, the IPG 14 includes pulse generation circuitry that provides electrical conditioning and stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), pulse rate (measured in pulses per second), and burst rate (measured as the stimulation on duration X and stimulation off duration Y).

Electrical stimulation will occur between two (or more) activated electrodes, one of which may be the IPG case. Simulation energy may be transmitted to the tissue in a monopolar or multipolar (e.g., bipolar, tripolar, etc.) fashion. Monopolar stimulation occurs when a selected one of the lead electrodes 26 is activated along with the case of the IPG 14, so that stimulation energy is transmitted between the selected electrode 26 and case. Bipolar stimulation occurs when two of the lead electrodes 26 are activated as anode and cathode, so that stimulation energy is transmitted between the selected electrodes 26. For example, an electrode on one lead 12 may be activated as an anode at the same time that an electrode on the same lead or another lead 12 is activated as a cathode. Tripolar stimulation occurs when three of the lead electrodes 26 are activated, two as anodes and the remaining one as a cathode, or two as cathodes and the remaining one as an anode. For example, two electrodes on one lead 12 may be activated as anodes at the same time that an electrode on another lead 12 is activated as a cathode.

The stimulation energy may be delivered between electrodes as monophasic electrical energy or multiphasic electrical energy. Monophasic electrical energy includes a series of pulses that are either all positive (anodic) or all negative (cathodic). Multiphasic electrical energy includes a series of pulses that alternate between positive and negative. For example, multiphasic electrical energy may include a series of biphasic pulses, with each biphasic pulse including a cathodic (negative) stimulation pulse and an anodic (positive) recharge pulse that is generated after the stimulation pulse to prevent charge build-up at the electrode-tissue interface, thereby avoiding electrode degradation and cell trauma. That is, charge is conveyed through the electrode-tissue interface via current at an electrode during a stimulation period (the length of the stimulation pulse), and then pulled back off the electrode-tissue interface via an oppositely polarized current at the same electrode during a recharge period (the length of the recharge pulse).

Figure 3:
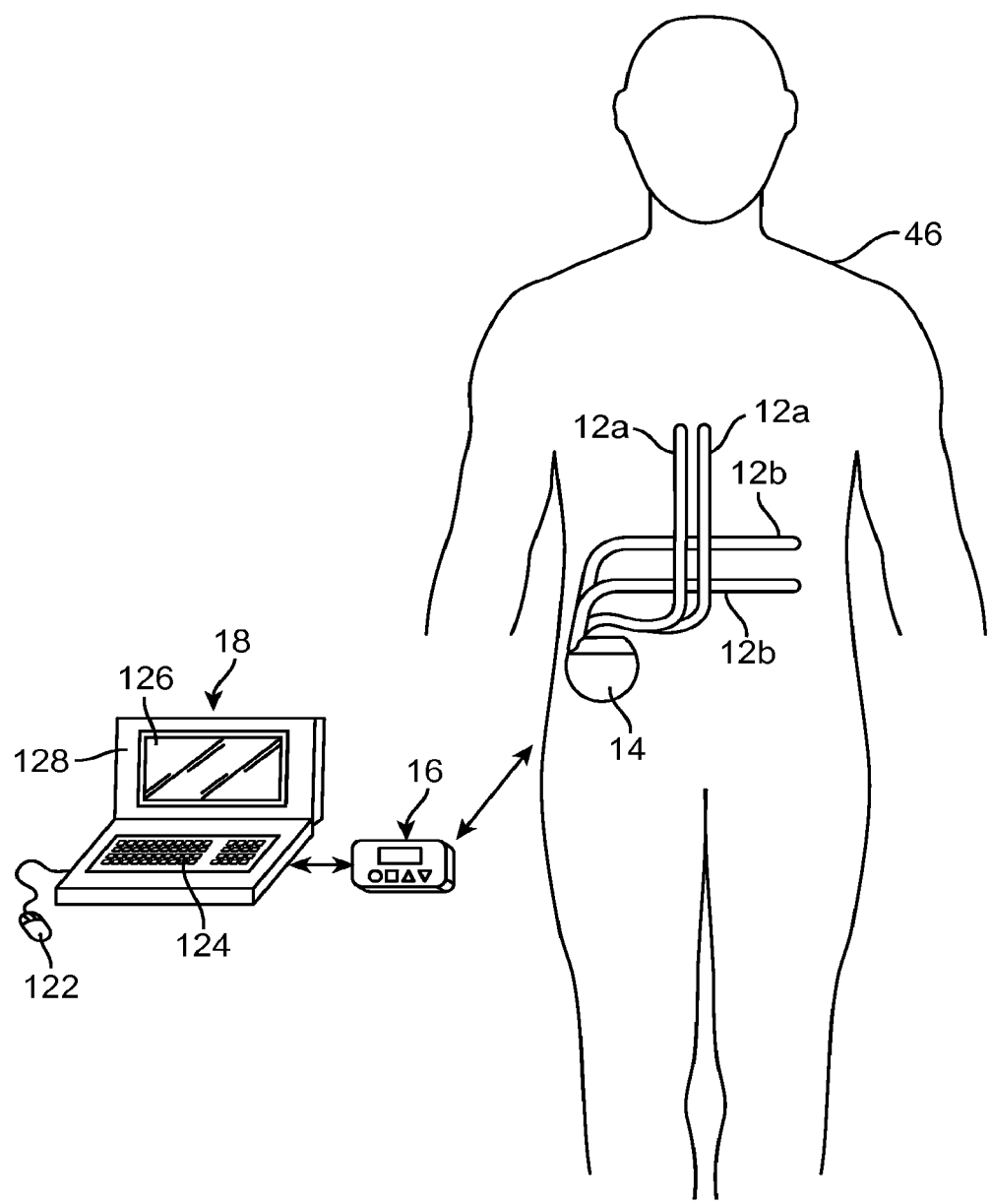
FIG. 3 is a plan view of the nerve tissue stimulation system of FIG. 1 in use with a patient.

For Spinal Cord Stimulation (SCS) applications, the percutaneous leads 12a are implanted within the spinal column of a patient 46, as shown in FIG. 3. The preferred placement of the stimulation leads 12a is adjacent, i.e., resting near, the spinal cord area to be stimulated. The percutaneous stimulation leads 12a can be introduced, with the aid of fluoroscopy, into the epidural space through a Touhy-like needle, which passes through the skin, between the desired vertebrae, and into the epidural space above the dura layer. For unilateral pain, one stimulation lead 12a is placed on the corresponding lateral side of the spinal cord. For bilateral pain, one stimulation lead 12a is placed down the midline of the spinal cord, or two stimulation leads 12a are placed down the respective sides of the midline. In many cases, a stylet, such as a metallic wire, is inserted into a lumen running through the center of each of the stimulation leads 12a to aid in insertion of the lead through the needle and into the epidural space. The stylet gives the lead rigidity during positioning, and once the stimulation lead 12a is positioned, the stylet can be removed after which the lead becomes flaccid. In the case where a surgical paddle lead is alternatively used in place of the percutaneous leads, it can be implanted within the spinal column using a surgical procedure, and specifically, a laminectomy, which involves removal of the laminar vertebral tissue to allow both access to the dura layer and positioning of the leads 12a.

For Peripheral Nerve Field Stimulation (PNFS) applications, the percutaneous stimulation leads 12b are implanted remotely from the spinal cord; for example, in the subcutaneous tissues of the lower back, directly in the region of maximum pain. As illustrated, the stimulation leads 12b are placed laterally (horizontally) across the back of the patient; for example, on both sides of the L4-L5 levels overlying the paraspinous muscles. For the purposes of this specification, peripheral nerve tissue is any nerve tissue that is not part of the central nervous system (i.e., nerve tissue other than the brain or spinal cord). In the illustrated embodiment, the stimulation leads 12b are implanted within the lower back of the patient. Alternatively, the stimulation leads 12b may be implanted in other regions of the patient where peripheral nerves can be stimulated, including the head (e.g., ONS) and cervical regions, abdomen, and limbs. The stimulation leads 12b may be implanted in the selected peripheral region using a Touhy-like needle that can be tunneled just under the dermis, with the proper positioning of the stimulation leads 12b being confirmed via fluoroscopy.

After proper placement of the stimulation leads 12 at the target areas of the spinal cord and peripheral regions, the leads 12 are anchored in place to prevent movement of the stimulation leads 12. To facilitate the location of the IPG 14 away from the exit point of the stimulation leads 12 implanted within the spinal column, the lead extensions 24 may be used. Whether lead extensions are used or not, the proximal ends of the stimulation leads 12 exiting the spinal column and the stimulation leads 12 implanted within the lower back region are passed through one or more tunnels (not shown) subcutaneously formed along the torso of the patient to a subcutaneous pocket (typically made in the patient's abdominal or buttock area) where the IPG 14 is implanted. The IPG 14 may, of course, also be implanted in other locations of the patient's body. A subcutaneous tunnel can be formed using a tunneling tool over which a tunneling straw may be threaded. The tunneling tool can be removed, the stimulation leads 12 threaded through the tunneling straw, and then the tunneling straw removed from the tunnel while maintaining the stimulation leads 12 in place within the tunnel.

The stimulation leads 12 are then connected directly to the IPG 14 by inserting the proximal ends of the stimulation leads 12 within connector ports located on the connector 42 of the IPG 12 or connected to lead extensions 24, which are then inserted into the connector ports of the IPG 14. In the illustrated embodiment, the IPG 14 has four connector ports corresponding to the four stimulation leads 12. The IPG 14 can then be operated to generate electrical pulses that are delivered, through the electrodes, to the targeted tissue, and in particular, the dorsal column and dorsal root fibers within the spinal cord and lower back region of the patient in a manner described in further detail below. As there shown, the CP 18 communicates with the IPG 14 via the RC 16, thereby providing a means to control and reprogram the IPG 14.

Figure 4:
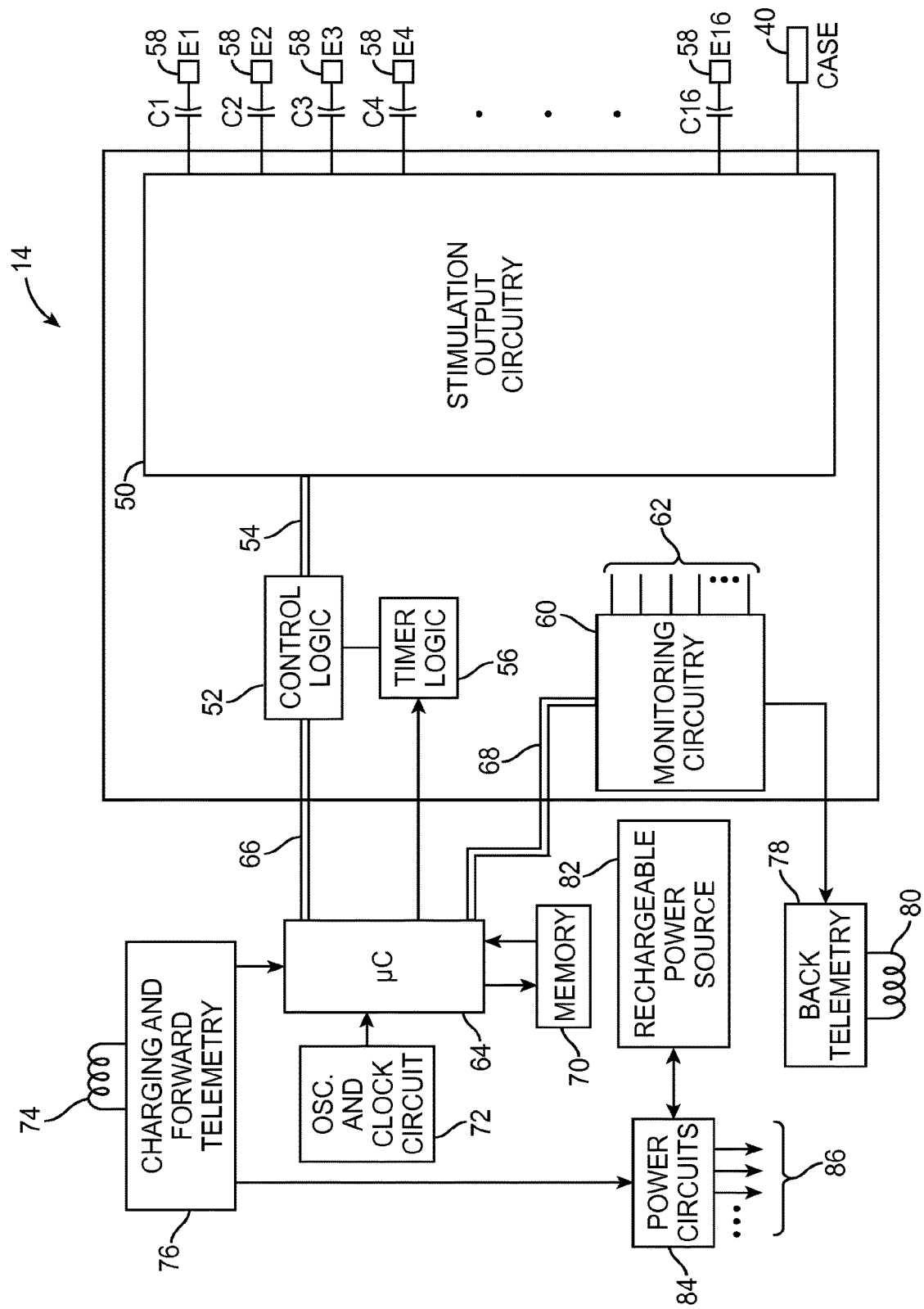
FIG. 4 is a block diagram of the internal components of the IPG of FIG. 1.

Turning next to FIG. 4, the main internal components of the IPG 14 will now be described. The IPG 14 includes stimulation output circuitry 50 configured for generating electrical stimulation energy in accordance with a defined pulsed waveform having a specified pulse amplitude, pulse rate, pulse width, pulse shape, and burst rate under control of control logic 52 over data bus 54. Control of the pulse rate and pulse width of the electrical waveform is facilitated by timer logic circuitry 56, which may have a suitable resolution, e.g., 10 µs. The stimulation energy generated by the stimulation output circuitry 50 is output via capacitors C1-C16 to electrical terminals 58 corresponding to the electrodes 26.

The analog output circuitry 50 may either comprise independently controlled current sources for providing stimulation pulses of a specified and known amperage to or from the electrodes 26, or independently controlled voltage sources for providing stimulation pulses of a specified and known voltage at the electrodes 26. The operation of this analog output circuitry, including alternative embodiments of suitable output circuitry for performing the same function of generating stimulation pulses of a prescribed amplitude and width, is described more fully in U.S. Pat. Nos. 6,516,227 and 6,993,384, which are expressly incorporated herein by reference.

The IPG 14 also comprises monitoring circuitry 60 for monitoring the status of various nodes or other points 62 throughout the IPG 14, e.g., power supply voltages, temperature, battery voltage, and the like. Notably, the electrodes 26 fit snugly within the tissue of the patient, and because the tissue is conductive, electrical measurements can be taken from the electrodes 26. Significantly, the monitoring circuitry 60 is configured for taking such electrical measurements, so that, as will be described in further detail below, the location and/or depth of each stimulation lead 12 within the patient may be determined.

Electrical signals can be transmitted between electrodes carried by one of the stimulation lead 12 and one or more other electrodes (e.g., electrodes on the same stimulation lead 12, electrodes on the other stimulation lead 12, the case 40 of the IPG 12, or an electrode affixed to the tissue), and then electrical parameters can be measured in response to the transmission of the electrical signals. In the illustrated embodiment, the electrical measurements taken by the monitoring circuitry 60 for the purpose of determining the location and/or depth of each stimulation lead 12 are electrical impedances, although other suitable measurements, such as, e.g., electrical field potentials or evoked potential measurements, can be obtained.

Electrical data can be measured using any one of a variety means. For example, the electrical data measurements can be made on a sampled basis during a portion of the time while the electrical stimulus pulse is being applied to the tissue, or immediately subsequent to stimulation, as described in U.S. patent application Ser. No. 10/364,436, which has previously been incorporated herein by reference. Alternatively, the electrical data measurements can be made independently of the electrical stimulation pulses, such as described in U.S. Pat. Nos. 6,516,227 and 6,993,384, which are expressly incorporated herein by reference. For example, electrical data measurements can be made in response to alternating current (AC) or pulsatile electrical signals, which preferably use amplitudes and pulsewidths (e.g., 1 mA for 20 µs) that generate no physiological response for the patient (i.e., subthreshold), but can alternatively be performed in response to stimulation pulses.

The impedance measurement technique may be performed by measuring impedance vectors, which can be defined as impedance values measured between selected pairs of electrodes 26. The interelectrode impedance may be determined in various ways. For example, a known current can be applied between a pair of electrodes 26, a voltage between the electrodes 26 can be measured, and an impedance between the electrodes 26 can be calculated as a ratio of the measured voltage to known current. Or a known voltage can be applied between a pair of electrodes 26, a current between the electrodes 26 can be measured, and an impedance between the electrodes 26 can be calculated as a ratio of the known voltage to measured current.

The field potential measurement technique may be performed by generating an electrical field at selected ones of the electrodes 26 using constant current and recording the electrical field at other selected ones of the lead electrodes 26. This may be accomplished in one of a variety of manners. For example, an electrical field may be generated by conveying electrical energy to a selected one of the electrodes 26 and returning the electrical energy at the IPG case 40. Alternatively, multipolar configurations (e.g., bipolar or tripolar) may be created between the lead electrodes 26. Or, an electrode that is sutured (or otherwise permanently or temporarily attached (e.g., an adhesive or gel-based electrode) anywhere on the patient's body may be used in place of the case IPG outer case or lead electrodes 26. In either case, while a selected one of the electrodes 26 is activated to generate the electrical field, a selected one of the electrodes 26 (which may include the activated electrode or another electrode) is operated to record the voltage potential of the electrical field. Alternatively, a differential field potential measurement between a pair of electrodes that are different from the electrodes that source and return the energy can be taken.

The evoked potential measurement technique may be performed by generating an electrical field at one of the electrodes 26, which is strong enough to depolarize the neurons adjacent the stimulating electrode beyond a threshold level, thereby inducing the firing of action potentials (APs) that propagate along the neural fibers. Such stimulation is preferably supra-threshold, but not uncomfortable. A suitable stimulation pulse for this purpose is, for example, 4 mA for 200 µS. While a selected one of the electrodes 26 is activated to generate the electrical field, a selected one or ones of the electrodes 26 (different from the activated electrode) is operated to record a measurable deviation in the voltage caused by the evoked potential due to the stimulation pulse at the stimulating electrode.

Further details discussing the measurement of electrical parameter data, such as electrode impedance, field potential, and evoked action potentials are set forth in U.S. patent application Ser. No. 10/364,436, entitled "Neural Stimulation System Providing Auto Adjustment of Stimulus Output as a Function of Sensed Impedance," U.S. patent application Ser. No. 10/364,434, entitled "Neural Stimulation System Providing Auto Adjustment of Stimulus Output as a Function of Sensed Pressure Changes," U.S. Pat. No. 6,993,384, entitled "Apparatus and Method for Determining the Relative Position and Orientation of Stimulation Leads," and U.S. patent application Ser. No. 11/096,483, entitled "Apparatus and Methods for Detecting Migration of Stimulation Leads," which are expressly incorporated herein by reference.

The IPG 14 further comprises processing circuitry in the form of a microcontroller (µC) 64 that controls the control logic 52 over data bus 66, and obtains status data from the monitoring circuitry 60 via data bus 68. The IPG 14 additionally controls the timer logic 56. The IPG 14 further comprises memory 70 and oscillator and clock circuit 72 coupled to the microcontroller 64. The microcontroller 64, in combination with the memory 70 and oscillator and clock circuit 72, thus comprise a microprocessor system that carries out a program function in accordance with a suitable program stored in the memory 70. Alternatively, for some applications, the function provided by the microprocessor system may be carried out by a suitable state machine.

Thus, the microcontroller 64 generates the necessary control and status signals, which allow the microcontroller 64 to control the operation of the IPG 14 in accordance with a selected operating program and stimulation parameters. In controlling the operation of the IPG 14, the microcontroller 64 is able to individually generate stimulus pulses at the electrodes 26 using the analog output circuitry 50, in combination with the control logic 52 and timer logic 56, thereby allowing each electrode 26 to be paired or grouped with other electrodes 26, including the monopolar case electrode, to control the polarity, amplitude, rate, pulse width and channel through which the current stimulus pulses are provided.

The IPG 14 further comprises an alternating current (AC) receiving coil 74 for receiving programming data (e.g., the operating program and/or stimulation parameters) from the RC 16 and/or CP 18 in an appropriate modulated carrier signal, and charging and forward telemetry circuitry 76 for demodulating the carrier signal it receives through the AC receiving coil 74 to recover the programming data, which programming data is then stored within the memory 70, or within other memory elements (not shown) distributed throughout the IPG 14.

The IPG 14 further comprises back telemetry circuitry 78 and an alternating current (AC) transmission coil 80 for sending informational data sensed through the monitoring circuitry 60 to the RC 16 and/or CP 18. The back telemetry features of the IPG 14 also allow its status to be checked. For example, when the RC 16 and/or CP 18 initiates a programming session with the IPG 14, the capacity of the battery is telemetered, so that the RC 16 and/or CP 18 can calculate the estimated time to recharge. Any changes made to the current stimulus parameters are confirmed through back telemetry, thereby assuring that such changes have been correctly received and implemented within the implant system. Moreover, upon interrogation by the RC 16 and/or CP 18, all programmable settings stored within the IPG 14 may be uploaded to the RC 16 and/or CP 18.

The IPG 14 further comprises a rechargeable power source 82 and power circuits 84 for providing the operating power to the IPG 14. The rechargeable power source 82 may, e.g., comprise a lithium-ion or lithium-ion polymer battery. The rechargeable battery 82 provides an unregulated voltage to the power circuits 84. The power circuits 84, in turn, generate the various voltages 86, some of which are regulated and some of which are not, as needed by the various circuits located within the IPG 14. The rechargeable power source 82 is recharged using rectified AC power (or DC power converted from AC power through other means, e.g., efficient AC-to-DC converter circuits, also known as "inverter circuits") received by the AC receiving coil 74. To recharge the power source 82, an external charger (not shown), which generates the AC magnetic field, is placed against, or otherwise adjacent, to the patient's skin over the implanted IPG 14. The AC magnetic field emitted by the external charger induces AC currents in the AC receiving coil 74. The charging and forward telemetry circuitry 76 rectifies the AC current to produce DC current, which is used to charge the power source 82. While the AC receiving coil 74 is described as being used for both wirelessly receiving communications (e.g., programming and control data) and charging energy from the external device, it should be appreciated that the AC receiving coil 74 can be arranged as a dedicated charging coil, while another coil, such as coil 80, can be used for bi-directional telemetry.

Additional details concerning the above-described and other IPGs may be found in U.S. Pat. No. 6,516,227, U.S. Patent Publication No. 2003/0139781, and U.S. patent application Ser. No. 11/138,632, entitled "Low Power Loss Current Digital-to-Analog Converter Used in an Implantable Pulse Generator," which are expressly incorporated herein by reference. It should be noted that rather than an IPG, the system 10 may alternatively utilize an implantable receiver-stimulator (not shown) connected to leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

Figure 5:
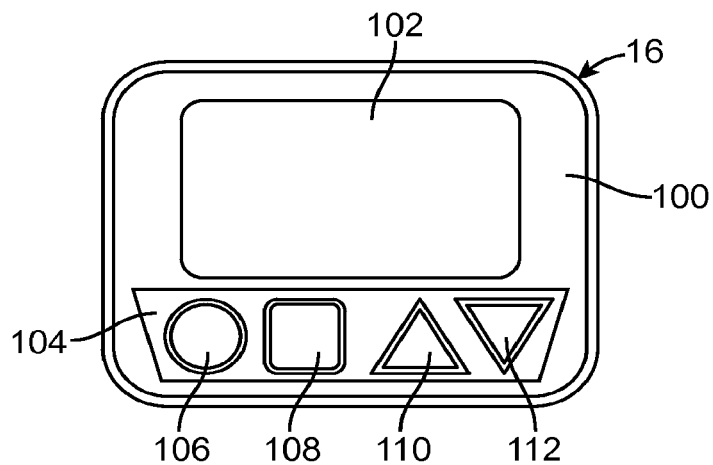
FIG. 5 is front view of a remote control (RC) used in the nerve tissue stimulation system of FIG. 1.

Referring now to FIG. 5, one exemplary embodiment of an RC 16 will now be described. As previously discussed, the RC 16 is capable of communicating with the IPG 14, CP 18, or ETS 20. The RC 16 comprises a casing 100, which houses internal componentry (including a printed circuit board (PCB)), and a lighted display screen 102 and button pad 104 carried by the exterior of the casing 100. In the illustrated embodiment, the display screen 102 is a lighted flat panel display screen, and the button pad 104 comprises a membrane switch with metal domes positioned over a flex circuit, and a keypad connector connected directly to a PCB. In an optional embodiment, the display screen 102 has touch screen capabilities. The button pad 104 includes a multitude of buttons 106, 108, 110, and 112, which allow the IPG 14 to be turned ON and OFF, provide for the adjustment or setting of stimulation parameters within the IPG 14, and provide for selection between screens.

In the illustrated embodiment, the button 106 serves as an ON/OFF button that can be actuated to turn the IPG 14 ON and OFF. The button 108 serves as a select button that allows the RC 16 to switch between screen displays and/or parameters. The buttons 100 and 112 serve as up/down buttons that can be actuated to increment or decrement any of stimulation parameters of the pulse generated by the IPG 14, including pulse amplitude, pulse width, and pulse rate. For example, the selection button 108 can be actuated to place the RC 16 in a "Pulse Amplitude Adjustment Mode," during which the pulse amplitude can be adjusted via the up/down buttons 110, 112, a "Pulse Width Adjustment Mode," during which the pulse width can be adjusted via the up/down buttons 110, 112, and a "Pulse Rate Adjustment Mode," during which the pulse rate can be adjusted via the up/down buttons 110, 112. Alternatively, dedicated up/down buttons can be provided for each stimulation parameter. Rather than using up/down buttons, any other type of actuator, such as a dial, slider bar, or keypad, can be used to increment or decrement the stimulation parameters. Further details of the functionality and internal componentry of the RC 16 are disclosed in U.S. Pat. No. 6,895,280, which has previously been incorporated herein by reference.

Figure 6:
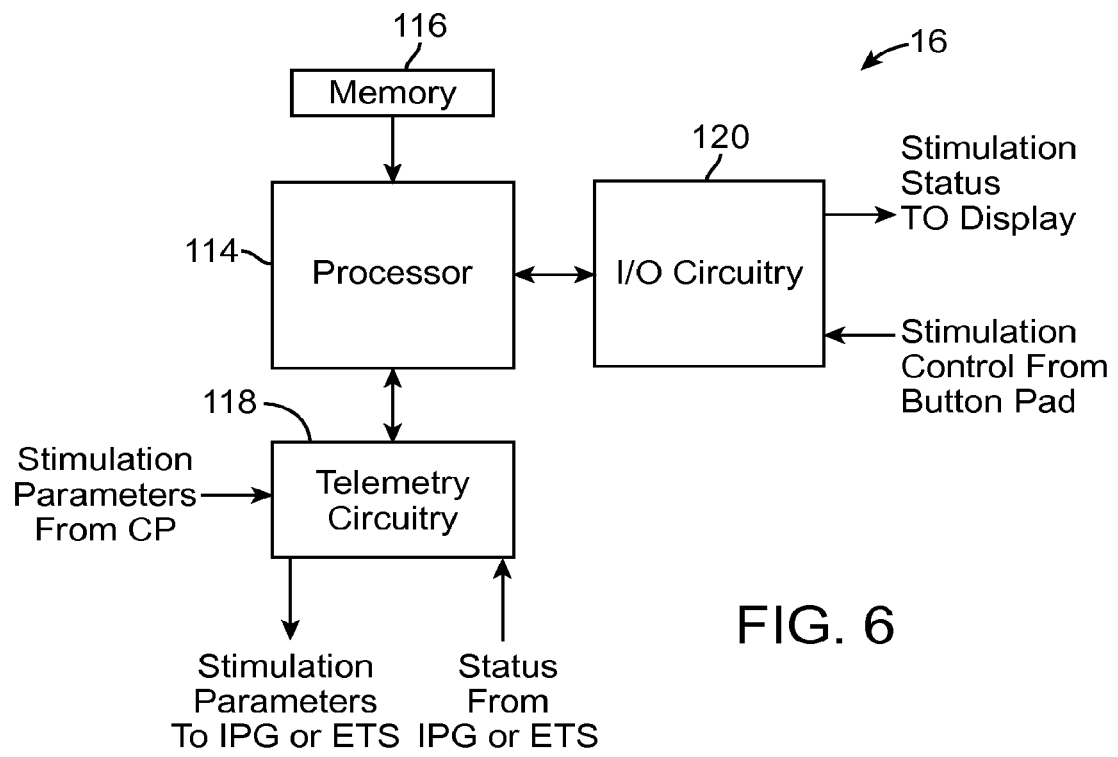
FIG. 6 is a block diagram of the internal components of the RC of FIG. 5.

Referring to FIG. 6, the internal components of an exemplary RC 16 will now be described. The RC 16 generally includes a processor 114 (e.g., a microcontroller), memory 116 that stores an operating program for execution by the processor 114, as well as stimulation parameter sets in a navigation table (described below), input/output circuitry, and in particular, telemetry circuitry 118 for outputting stimulation parameters to the IPG 14 and receiving status information from the IPG 14, and input/output circuitry 70 for receiving stimulation control signals from the button pad 104 and transmitting status information to the display screen 102 (shown in FIG. 5). As well as controlling other functions of the RC 16, which will not be described herein for purposes of brevity, the processor 114 generates new stimulation parameter sets in response to the user operation of the button pad 104. These new stimulation parameter sets would then be transmitted to the IPG 14 via the telemetry circuitry 118. Further details of the functionality and internal componentry of the RC 16 are disclosed in U.S. Pat. No. 6,895,280, which has previously been incorporated herein by reference.

As briefly discussed above, the CP 18 greatly simplifies the programming of multiple electrode combinations, allowing the user (e.g., the physician or clinician) to readily determine the desired stimulation parameters to be programmed into the IPG 14, as well as the RC 16. Thus, modification of the stimulation parameters in the programmable memory of the IPG 14 after implantation is performed by a user using the CP 18, which can directly communicate with the IPG 14 or indirectly communicate with the IPG 14 via the RC 16. That is, the CP 18 can be used by the user to modify operating parameters of the electrode array 26 near the spinal cord.

As shown in FIG. 3, the overall appearance of the CP 18 is that of a laptop personal computer (PC), and in fact, may be implanted using a PC that has been appropriately configured to include a directional-programming device and programmed to perform the functions described herein. Alternatively, the CP 18 may take the form of a mini-computer, personal digital assistant (PDA), smartphone, etc., or even a remote control (RC) with expanded functionality. Thus, the programming methodologies can be performed by executing software instructions contained within the CP 18. Alternatively, such programming methodologies can be performed using firmware or hardware. In any event, the CP 18 may actively control the characteristics of the electrical stimulation generated by the IPG 14 to allow the optimum stimulation parameters to be determined based on patient response and feedback and for subsequently programming the IPG 14 with the optimum stimulation parameters.

To allow the user to perform these functions, the CP 18 includes a mouse 122, a keyboard 124, and a programming display screen 126 housed in a housing 128. It is to be understood that in addition to, or in lieu of, the mouse 122, other directional programming devices may be used, such as a joystick, a button pad, a group of keyboard arrow keys, a roller ball tracking device, and horizontal and vertical rocker-type arm switches. The CP 18 further includes detection circuitry (not shown) capable of detecting an actuation event on the display screen 126. Such actuation event may include placing at least one pointing element (not shown) in proximity to at least one graphical object displayed on the display screen 126, as well as possibly other events involving the point element(s), such as moving the pointing element(s) across the screen or clicking or tapping with the pointing element(s), as will be described in further detail below.

In the preferred embodiments described below, the display screen 126 takes the form of a digitizer touch screen, which may either passive or active. If passive, the detection circuitry recognizes pressure or a change in an electrical current when a passive device, such as a finger or non-electronic stylus, contacts the screen. If active, the detection circuitry recognizes a signal transmitted by an electronic pen or stylus. In either case, the detection circuitry is capable of detecting when a physical pointing device (e.g., a finger, a non-electronic stylus, or an electronic stylus) is in close proximity to the screen, whether it be making physical contact between the pointing device and the screen or bringing the pointing device in proximity to the screen within a predetermined distance, as well as detecting the location of the screen in which the physical pointing device is in close proximity. In some embodiments, the display screen 126 takes the form of a conventional screen, in which case, the pointing element is not an actual pointing device like a finger or stylus, but rather is a virtual pointing device, such as a cursor controlled by a mouse, joy stick, trackball, etc.

Figure 7:
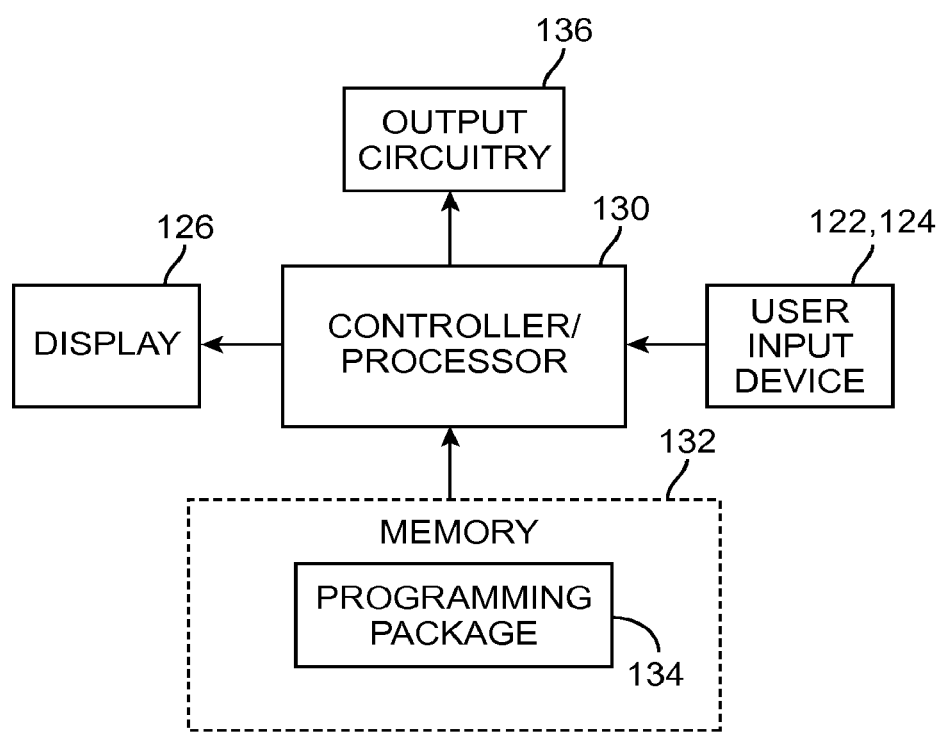
FIG. 7 is a block diagram of the internal components of a clinician's programmer (CP) used in the nerve tissue stimulation system of FIG. 1.

As shown in FIG. 7, the CP 18 further includes a controller/processor 130 (e.g., a central processor unit (CPU)) and memory 132 that stores a stimulation programming package 134, which can be executed by the controller/processor 130 to allow the user to program the IPG 14, and RC 16. Notably, while the controller/processor 130 is shown as a single device, the processing functions and controlling functions can be performed by a separate controller and processor. Thus, it can be appreciated that the controlling functions described below as being performed by the CP 18 can be performed by a controller, and the processing functions described below as being performed by the CP 18 can be performed by a processor. The CP 18 further includes output circuitry 136 (e.g., via the telemetry circuitry of the RC 16) for downloading stimulation parameters to the IPG 14 and RC 16 and for uploading stimulation parameters already stored in the memory 66 of the RC 16, via the telemetry circuitry 68 of the RC 16.

Execution of the programming package 134 by the controller/processor 130 provides a multitude of display screens (not shown) that can be navigated through via use of the mouse 122. These display screens allow the clinician to, among other functions, to select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), generate a pain map of the patient, define the configuration and orientation of the leads, initiate and control the electrical stimulation energy output by the leads 12, and select and program the IPG 14 with stimulation parameters in both a surgical setting and a clinical setting. Further details discussing the above-described CP functions are disclosed in U.S. patent application Ser. No. 12/501,282, entitled "System and Method for Converting Tissue Stimulation Programs in a Format Usable by an Electrical Current Steering Navigator," and U.S. patent application Ser. No. 12/614,942, entitled "System and Method for Determining Appropriate Steering Tables for Distributing Stimulation Energy Among Multiple Stimulation Electrodes," which are expressly incorporated herein by reference.

Significantly, the programming package 134 identifies which configuration of stimulation leads 12 connected to the IPG 14 is implanted in the epidural space of the patient for SCS therapy and which configuration of stimulation leads 12 connected to the IPG 14 is implanted in the subcutaneous tissues of the patient for PNFS therapy. The programming package 134 also determines the implantation depth of the stimulation leads 12 within the patient. Knowledge of which region of the patient in which each stimulation configuration is implanted and the implant depth of each stimulation lead 12 can be useful for enabling efficient programming of the IPG 14 and estimation of the stimulation outcome.

The location and depth information of the stimulation leads 12 are determined using an electrically-based technique. In particular, the electrical parameter data measured by the monitoring circuitry 60 (shown in FIG. 4) reflects the variation in electric properties and medium boundary. That is, due to the difference in anatomy and tissue composition, electric properties and medium boundary conditions can be different at different locations in the body, resulting in different electric field distributions. Even at a particular body location, due to the tissue composition and structure, different subdermal layers can have different electrical properties, and especially the distance to the skin surface can result in different boundary conditions when electrical current flows in the tissue media and generates electric field potentials. The combined effect of electrical properties and boundary conditions can be reflected in the electric impedances that can be directly obtained from measured impedance data or indirectly implied from other types of measured electrical parameter data.

The controller/processor 130 uses the measured electrical parameter data, along with any other information input by the user or otherwise acquired by the CP 18, to help identify the region of the body in which each stimulation lead configuration is implanted.

For example, tissue impedance measured by a stimulation lead implanted within an epidural space may be in the range of hundreds of ohms (e.g., 200-600 ohms), whereas tissue impedance measured by a stimulation lead implanted within a peripheral region of the patient may be in the range of several hundred to thousand ohms (e.g., 600-2000 ohms). Thus, if the measured electrical parameter data indicates a tissue impedance of a few hundred ohms, the implantation site of the stimulation lead configuration may be determined to be in the epidural space, thereby requiring a stimulation regimen conducive to SCS therapy. In contrast, if the measured electrical parameter data indicates a tissue impedance of around a thousand ohms or above, the implantation site of the stimulation lead configuration may be determined to be in a peripheral region of the patient, thereby requiring a stimulation regimen conducive to PNFS therapy.

As another example, electrical parameter measurements indicating the tissue impedance between the stimulation leads of a particular configuration may be taken to determine the relative distance between the stimulation leads. Because stimulation leads implanted within an epidural space are generally spaced closed to each other, the inter-lead impedance will typically be relatively small in this case, thus, indicative that these leads are implanted within the epidural space, thereby requiring a stimulation regimen conducive to SCS therapy. In contrast, because stimulation leads implanted within subcutaneous tissue are generally spaced far from each other, the inter-lead impedance will typically be relatively large in this case, thus, indicative that these leads are subcutaneously implanted, thereby requiring a stimulation regimen conducive to PNFS therapy.

Figure 8:
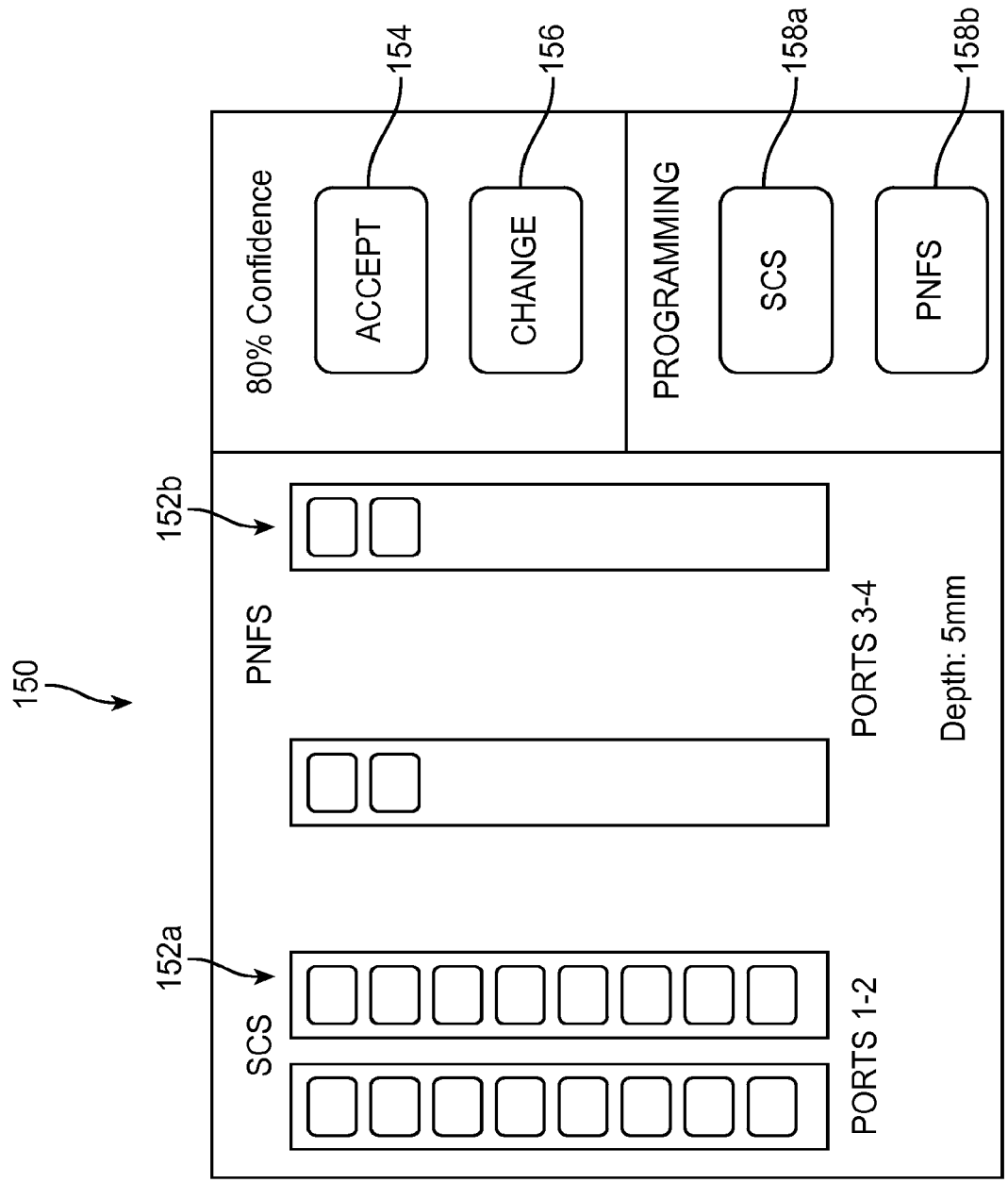
FIG. 8 is a plan view of a lead configuration screen generated by the CP of FIG. 7.

Referring to FIG. 8, the controller/processor 130 conveys the estimated location of the stimulation lead configuration to the user via a lead configuration screen 150, which displays two different graphical lead configurations: an SCS lead configuration 152a and a PNFS lead configuration 152b. The CP 18 optionally computes a confidence rating (in this case, a confidence percentage) that the stimulation lead configuration associated with the epidural space or subcutaneous tissue is coupled to a particular set of connector ports in the IPG 14, and then displays the confidence rating underneath the graphical lead configurations 12'. In the illustrated embodiment, a confidence rating of 80% is shown. The lead configuration screen 150 includes an "ACCEPT" graphical control icon 154 that can be actuated by the user to confirm the lead configuration location, and a "CHANGE" graphical control icon 156 that manually changes the lead configuration location.

Figure 9A:
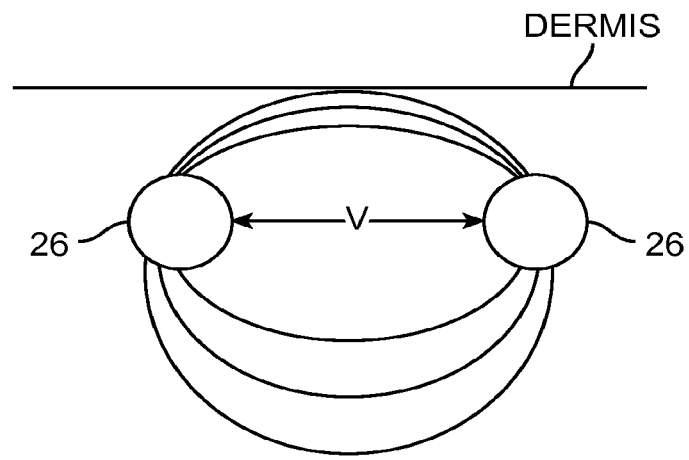
FIG. 9*a* is a plan view illustrating current flowing between electrodes implanted shallow within the subcutaneous tissue of the patient.
Figure 9B:
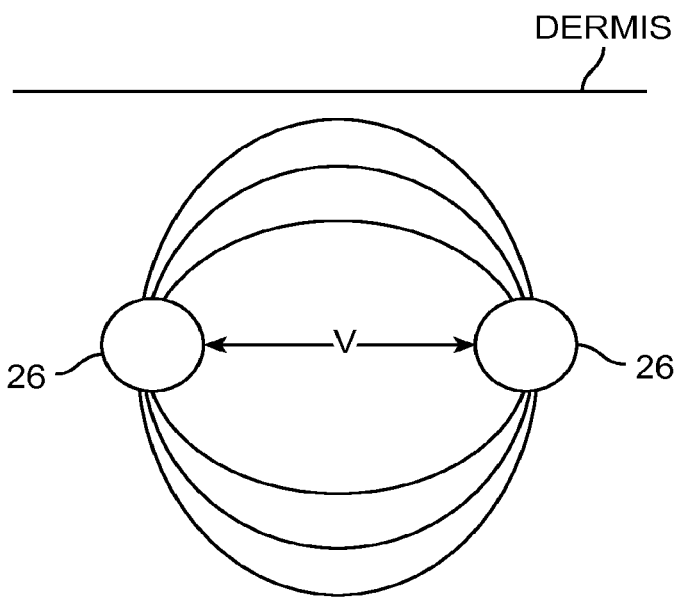
FIG. 9*b* is a plan view illustrating current flowing between electrodes implanted deep within the subcutaneous tissue of the patient.

The controller/processor 130 also uses the measured electrical parameter data to help determine the depth in which each of the stimulation leads 12b is subcutaneously implanted within the patient. For example, as illustrated in FIG. 9a, electrodes 26 implanted relatively shallow in tissue cause current "crowding" at the dermis, thereby resulting in a relatively high impedance between the electrodes 26. In contrast, as illustrated in FIG. 9b, electrodes implanted relatively deep in the tissue cause generally more homogenous current flow, thereby resulting in a relatively low impedance between the electrodes 26. Thus, impedance measured from a superficial dermis layer may have a higher value, impedance measured from a subcutaneous layer may have a lower value, and impedance measured from a deeper muscle layer may have an even lower value (due to depth and the higher conductivity of muscle). Based on the principal that impedance between two electrodes decreases as they are implanted more deeply in the tissue, the CP 18 computes the depth of each of the stimulation leads 12b and displays the depth value underneath the graphical PNFS lead configuration 152b in FIG. 8. The depth value may be an absolute value, relative value, or normalized value.

Notably, tissue impedances vary from individual to individual, and therefore, it may be useful to obtain a reference impedance value from each individual in order to evaluate the relative impedance measured from the subcutaneous leads 12b. For example, a transcutaneous bipolar impedance may be measured from the surface of the pinched skin (wed skin or conductive gel applied to the skin) in the region where the stimulation leads 12b are implanted. If a relationship between the transcutaneous reference impedance and the depth-dependent stimulation leads 12b can be established, the former may be used as a reference to evaluate the impedance measured from the subcutaneous stimulation leads 12b.

Figure 10A:
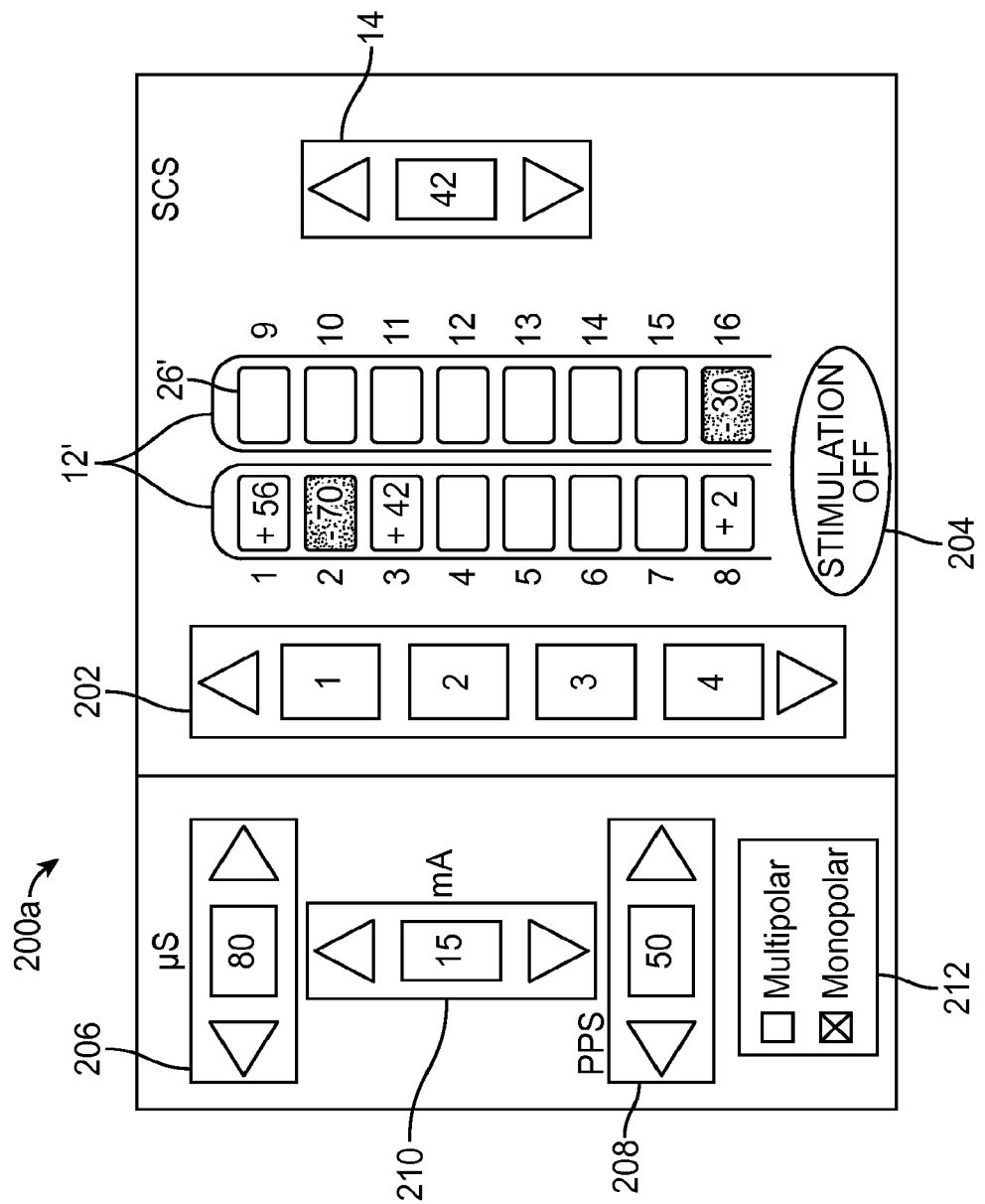
FIG. 10*a* is a plan view of an SCS programming screen generated by the CP of FIG. 7 for programming the IPG of FIG. 3.
Figure 10B:
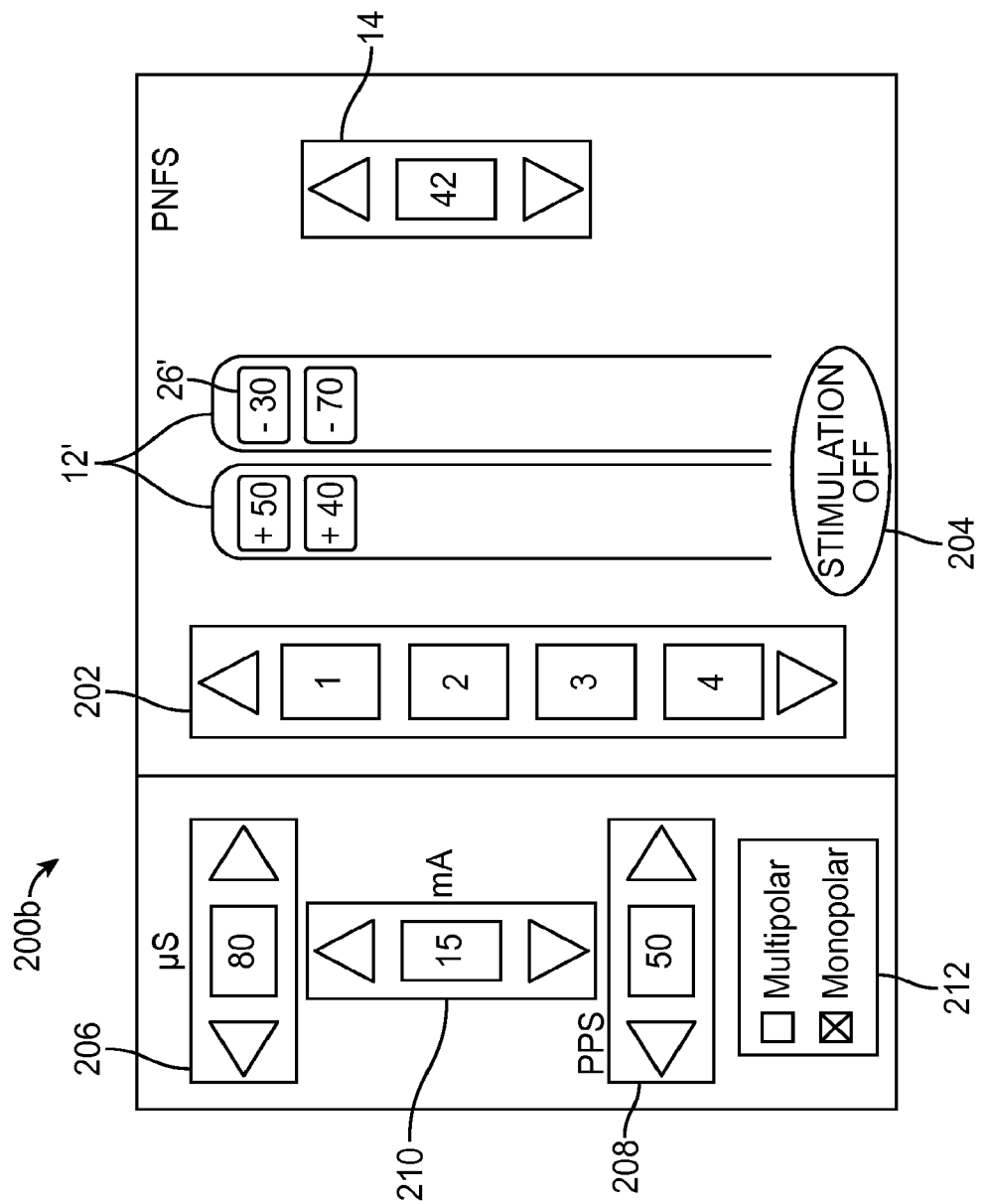
FIG. 10*b* is a plan view of an PNFS programming screen generated by the CP of FIG. 7 for programming the IPG of FIG. 3.

The lead configuration screen 150 further includes an SCS programming control icon 158a, which can be actuated by the user to enable the display of an SCS programming screen 200a (shown in FIG. 10a), and a PNFS programming control icon 158b, which can be actuated by the user to enable the display of a PNFS programming screen 200b (shown in FIG. 10b). The programming screens 200a, 200b include various control elements described below that can be actuated to perform various control functions.

Each of the programming screens 200a, 200b includes an electrode combination control 202 having arrows that can be actuated by the user to select one of four different electrode combinations 1-4. Each of the programming screens 200a, 200b further includes a stimulation on/off control 204 that can be alternately actuated initiate or cease the delivery of electrical stimulation energy from the IPG 14 via the selected electrode combination.

Each of the programming screens 200a, 200b further includes various stimulation parameter controls that can be operated by the user to manually adjust stimulation parameters for the selected electrode combination. In particular, each of the programming screens 200a, 200b includes a pulse width adjustment control 206 (expressed in microseconds (μs)), a pulse rate adjustment control 208 (expressed in Hertz (Hz)), and a pulse amplitude adjustment control 210 (expressed in milliamperes (mA)). Each control includes a first arrow that can be actuated to decrease the value of the respective stimulation parameter and a second arrow that can be actuated to increase the value of the respective stimulation parameter.

Each of the electrode combinations 1-4 can be created using various control elements. In particular, each of the programming screens 200a, 200b displays graphical representations of the leads 12' including the electrodes 26'. In the illustrated embodiment, each electrode representation 26' takes the form of a closed geometric figure, and in this case a rectangle. In alternative embodiments, the electrode representations 26' can take the form of other types of closed geometric figures, such as circles. The electrode representations 26' can be actuated multiple times to switch the corresponding active electrode 26 between a positive polarity (anode), a negative polarity (cathode), and an off-state. In essence, the electrode representations 26' themselves operate as the graphical control elements, the actuations of which prompt the controller/processor 130 to assign the polarities to the selected electrodes 26. In alternative embodiments, control elements separate from the electrode representations 26' may be used to change the polarity of the selected electrodes 26.

To enable selection between a multipolar configuration and a monopolar configuration, each of the programming screens 200a, 200b also includes multipolar/monopolar stimulation selection control 212, which includes check boxes that can be alternately actuated by the user to selectively provide multipolar or monopolar stimulation. If a multipolar electrode arrangement is desired, at least one of the electrodes E1-E16 will be selected as an anode (+) and at least one other of the electrodes E1-E16 will be selected as a cathode (−). If a monopolar electrode arrangement is desired, none of the electrodes E1-E16 will be selected as one polarity (e.g., an anode (+)), and thus, the electrode presentations 26' can only be actuated to toggle the corresponding electrode 26 between the other polarity (e.g., a cathode (−)) and off (0).

Each of the programming screens 200a, 200b further includes an electrode specific current adjustment control 214 that can be manipulated to independently vary stimulation amplitude values for the electrodes E1-E16. In particular, for each electrode selected to be activated as either a cathode or anode, the clinician can actuate the upper arrow of the control 214 to incrementally increase the absolute value of the stimulation amplitude of the selected electrode, and the clinician can actuate the lower arrow of the control 214 to incrementally decrease the absolute value of the stimulation amplitude of the selected electrode. The control 214 also includes an indicator that provides an alphanumeric indication of the stimulation amplitude currently assigned to the selected electrode. In an optional embodiment, non-alphanumeric indicators, such as different colors, different color luminances, different patterns, different textures, different partially-filled objects, etc., can be used to indicate the stimulation amplitude currently assigned to the selected electrodes, as discussed in U.S. patent application Ser. No. 13/200,629, entitled "Stimulation System and Method for Graphically Displaying Electrode Stimulation Values," which is expressly incorporated herein by reference.

In the illustrated embodiments, the stimulation amplitude values are fractionalized electrical current values (% current), such that the values for each polarity totals to 100. However, in alternative embodiments, the stimulation amplitude values may be normalized current or voltage values (e.g., 1-10), absolute current or voltage values (e.g., mA or V), etc. Furthermore, the stimulation amplitude values may be parameters that are a function of current or voltage, such as charge (current amplitude×pulse width) or charge injected per second (current amplitude×pulse width× rate (or period)).

In alternative embodiments, a stimulation amplitude adjustment control (not shown) may appear next to the electrode representation 26' that has been actuated, as described in U.S. patent application Ser. No. 13/200,629, which has been previously incorporated herein by reference, or may be superimposed over the electrode representation 26' that has been actuated, as described in U.S. Provisional Patent Application Ser. No. 61/486,141, entitled "Stimulation System with On-Effector Programmer Control," which is expressly incorporated herein by reference.

In alternative embodiments, each of the programming screens 200a, 200b facilitates automated current steering; for example, by allowing the user to switch between a manual mode using the electrode selection and current adjustment techniques described above, an electronic trolling ("e-troll") mode that quickly sweeps the electrode array using a limited number of electrode configurations to gradually move a cathode in bipolar stimulation, and a Navigation programming mode that finely tunes and optimizes stimulation coverage for patient comfort using a wide number of electrode configurations, as described in U.S. Provisional Patent Application Ser. No. 61/576,924, entitled "Seamless Integration of Different Programming Modes for a Neurostimulator Programming System," which is expressly incorporated herein by reference. Virtual target poles may be utilized to steer the current within the electrode array, as described in U.S. Provisional Patent Application Ser. No. 61/452,965, entitled "Stimulation System for Defining a Generalized Virtual Multipole," which is expressly incorporated herein by reference.

As can be seen, the programming screens 200a, 200b differ from each other in that the SCS programming screen 200a includes sixteen electrode representations 26' arranged in two columns to emulate the electrodes of the SCS stimulation leads 12a, whereas the SCS programming screen 200b includes four electrode representations 26' arranged in two columns to emulate the electrodes of the PNFS stimulation leads 12b. The CP 18 also allows electrode interactions that appropriate for the intended therapy. For example, for the SCS stimulation leads 12a, the electrodes can be independently programmed such that any electrode can be programmed as a cathode or an anode irrespective of the polarity of the other electrodes. In contrast, for the PNFS stimulation leads 12b, the electrodes of any particular lead must be programmed to have the same polarity (e.g., the anodes will be confined to one stimulation lead, while the cathodes are confined to the other stimulation lead). Thus, in the SCS programming screen 200a, the electrode representations 26' may be operated independently from each other, such that electrodes 26 on the same lead can have different polarities, whereas, in the PNFS programming screen 200b, the electrode representations 26' can only be globally operated for each lead, such that electrodes 26 on the same lead are forced to have the same polarity.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A system comprising an external control device configured for use with a stimulation device capable of delivering an electrical signal to a stimulation lead implanted in an anatomical location within a patient and measuring an electrical parameter in response to delivery of the electrical signal, the anatomical location being one of a plurality of anatomical locations in which the stimulation lead is capable of being implanted, the external control device comprising:
   telemetry circuitry configured to communicate with the stimulation device; and
   a processor configured to:
   receive a signal indicative of the measured electrical parameter from the stimulation device;
   implement a process dependent on the received signal to determine a programmable parameter set, wherein the programmable parameter set is dependent upon the anatomical location of the implanted stimulation lead, the measured electrical parameter being indicative of the anatomical location in which the stimulation lead is implanted; and
   program the stimulation device via the telemetry circuitry to deliver electrical stimulation energy using the stimulation lead according to the determined programmable parameter set.

2. The system of claim 1, further comprising the stimulation device.

3. The system of claim 1, wherein the electrical parameter is measured at another stimulation lead implanted within the patient.

4. The system of claim 1, wherein the processor is further configured to compare the measured electrical parameter to one or more threshold ranges, and to implement the process to determine the programmable parameter set based on the comparison.

5. The system of claim 1, wherein the anatomical location indicated by the measured electrical parameter corresponds to a spinal epidural space.

6. The system of claim 1, wherein the measured electrical parameter is indicative of a tissue impedance, the tissue impedance being indicative of the anatomical location of the implanted stimulation lead.

7. The system of claim 1, wherein the stimulation lead includes a plurality of electrodes, and the measured electrical parameter is indicative of a field potential measured at selected ones of the plurality of electrodes when an electric field is generated at other selected ones of the plurality of electrodes using a constant current, the field potential being indicative of the anatomical location of the implanted stimulation lead.

8. The system of claim 1, wherein the measured electrical parameter is indicative of an evoked potential from depolarized neurons, the evoked potential being indicative of the anatomical location of the implanted stimulation lead.

9. The system of claim 1, wherein the programmable parameter set includes an electrode combination dependent on the anatomical location of the implanted stimulation lead.

10. The system of claim 1, wherein the external control device further includes a user interface configured to display a plurality of different programming screens respectively associated with different anatomical regions of a patient, wherein the process implemented by the processor includes selecting one of the programming screens dependent on the received signal indicative of the measured electrical parameter, and receiving a user input through the selected programming screen for use in programming the programmable parameter set.

11. The system of claim 10, wherein:
the processor is further configured to compute a confidence rating for the plurality of different anatomical regions based on the measured electrical parameter; and
the user interface is further configured to identify the different anatomical regions and associated computed confidence rating, and to receive a user input for selecting one of the programming screens.

12. A method, comprising:
receiving, using a processor and telemetry circuitry, a signal indicative of a measured electrical parameter from a stimulation device, wherein the stimulation device is configured to deliver an electrical signal to a stimulation lead implanted at an anatomical location within a patient and measure the electrical parameter in response to delivery of the electrical signal, wherein the anatomical location is one of a plurality of anatomical locations in which the stimulation lead is capable of being implanted;
implementing a process, using the processor, dependent on the received signal to determine a programmable parameter set, wherein the programmable parameter set is dependent upon the anatomical location of the implanted stimulation lead as indicated by the measured electrical parameter; and
programming the stimulation device using the processor and the telemetry circuitry to deliver electrical stimulation energy using the stimulation lead according to the determined programmable parameter set.

13. The method of claim 12, further comprising delivering the electrical signal and measuring the electrical parameter using the stimulation device.

14. The method of claim 12, wherein the measured electrical parameter is indicative of a tissue impedance, the tissue impedance being indicative of the anatomical location of the implanted stimulation lead.

15. The method of claim 12, wherein the stimulation lead includes a plurality of electrodes, and the measured electrical parameter is indicative of a field potential measured at selected ones of the plurality of electrodes when an electric field is generated at other selected ones of the plurality of electrodes using a constant current, the field potential being indicative of the location of the implanted stimulation lead.

16. The method of claim 12, wherein the measured electrical parameter is indicative of an evoked potential from depolarized neurons, the evoked potential being indicative of the location of the implanted stimulation lead.

17. A non-transitory machine-readable medium including instructions, which when executed by a machine having telemetry circuitry and a processor, cause the machine to:
receive, using the processor and the telemetry circuitry, a signal indicative of a measured electrical parameter from a stimulation device, wherein the stimulation device is configured to deliver an electrical signal to a stimulation lead implanted at an anatomical location within a patient and measure the electrical parameter in response to delivery of the electrical signal, wherein the anatomical location is one of a plurality of anatomical locations in which the stimulation lead is capable of being implanted;
implement a process, using the processor, dependent on the received signal to determine a programmable parameter set, wherein the programmable parameter set is dependent upon the anatomical location of the implanted stimulation lead as indicated by the measured electrical parameter; and
program the stimulation device using the processor and the telemetry circuitry to deliver electrical stimulation energy using the stimulation lead according to the determined programmable parameter set.

18. The non-transitory machine-readable medium of claim 17, wherein the measured electrical parameter is indicative of a tissue impedance, the tissue impedance being indicative of the location of the implanted stimulation lead.

19. The non-transitory machine-readable medium of claim 17, wherein the stimulation lead includes a plurality of electrodes, and the measured electrical parameter is indicative of a field potential measured at selected ones of the plurality of electrodes when an electric field is generated at other selected ones of the plurality of electrodes using a constant current, the field potential being indicative of the location of the implanted stimulation lead.

20. The non-transitory machine-readable medium of claim 17, wherein the measured electrical parameter is indicative of an evoked potential from depolarized neurons, the evoked potential being indicative of the location of the implanted stimulation lead.

* * * * *